(12) United States Patent
Janus

(10) Patent No.: US 7,935,100 B2
(45) Date of Patent: May 3, 2011

(54) CELL CULTURE MEDIUM CONTAINER ASSEMBLY

(75) Inventor: Jeffrey Janus, Frederick, MD (US)

(73) Assignee: International Stem Cell Corporation, Oceanside, CA (US)

( * ) Notice: Subject to any disclaimer, the term of this patent is extended or adjusted under 35 U.S.C. 154(b) by 304 days.

(21) Appl. No.: 11/634,448

(22) Filed: Dec. 5, 2006

(65) Prior Publication Data
US 2007/0282293 A1 Dec. 6, 2007

Related U.S. Application Data

(60) Provisional application No. 60/742,795, filed on Dec. 5, 2005.

(51) Int. Cl.
*A61B 19/00* (2006.01)
(52) U.S. Cl. ............ 604/404; 604/403; 40/506; 40/312; 40/324; 40/661; 446/327; 446/321; 434/402; 434/427; 434/428; 206/459.5

(58) Field of Classification Search .................. 604/403, 604/404
See application file for complete search history.

(56) References Cited

U.S. PATENT DOCUMENTS

| | | | | |
|---|---|---|---|---|
| 2,818,071 | A * | 12/1957 | Barry | 604/46 |
| 4,051,265 | A | 9/1977 | Kirshenbaum et al. | 426/107 |
| 4,878,588 | A | 11/1989 | Ephraim | 215/11.2 |
| 5,282,583 | A * | 2/1994 | Hogberg | 242/420.3 |
| 5,342,093 | A * | 8/1994 | Weernink | 283/81 |
| 5,809,674 | A * | 9/1998 | Key | 40/306 |
| 6,113,857 | A | 9/2000 | Manico et al. | 422/61 |
| 6,613,036 | B1 * | 9/2003 | Farmer et al. | 604/408 |
| 7,172,065 | B2 * | 2/2007 | Prater | 206/5 |
| 2003/0129342 | A1 | 7/2003 | Hara et al. | 428/36.91 |
| 2004/0251159 | A1 | 12/2004 | Tingey et al. | 206/461 |

* cited by examiner

*Primary Examiner* — Tatyana Zalukaeva
*Assistant Examiner* — Susan S. Su
(74) *Attorney, Agent, or Firm* — DLA Piper LLP (US)

(57) ABSTRACT

A light sensitive media packaging with unique shrink-wrap light protection label that works as a light barrier to protect media from light damage.

10 Claims, 5 Drawing Sheets

Medium container completely covered with shrink-wrap label.
Perforations are around bottom of cap (dotted line).

Medium container completely covered with shrink-wrap label.
Perforations are around bottom of cap (dotted line).

First Production - Water Bath Bag

Media Container in Water Bath Bag

CELL CULTURE MEDIUM CONTAINER ASSEMBLY

CROSS REFERENCE TO RELATED APPLICATIONS

This application claims the benefit of U.S. Provisional Application No. 60/742,795 filed on Dec. 5, 2005, the contents of which are incorporated by reference.

FIELD OF THE INVENTION

The present invention pertains to the field of cell culture medium and more specifically to a cell culture medium container having a shrink-wrap light protection label for storing cell culture medium.

BACKGROUND INFORMATION

Cell culture medium is used to keep cells alive outside of an organism, usually in a laboratory (terminology is in vitro; Latin for "in glass"). It is composed of a sterile nutrient system; usually a complex mixture of organic and inorganic materials. Protein growth factors are usually added to promote cell growth or other specific behaviors. Supplements are added to protect the cells from microorganisms or stabilize the environment.

Cell culture media is generally stored in clear plastic or glass bottles with screw tops or in some cases, bags. Labeling commonly consists of a stick-on paper or plastic based label that covers a limited area of the container (generally less than 25 percent of the container's surface area).

Media is added to cells in liquid form. As living cells metabolize components of the medium critical components are depleted and waste products are produced, creating the need for frequent media replacement.

As a liquid, media should be stored at refrigeration temperatures and be shielded from light. Low temperatures decelerate the normal rates of protein denaturation that can deplete critical media components. Protection from visible light is necessary because light exposure leads to photoreactions involving riboflavin, thiols, metal ions and other components that can degrade the component and produce reactive oxygen species (ROS) that damage cells (see Grzelak et al., "Light-dependent generation of reactive oxygen species in cell culture media", Free Radic. Biol. Med. 12:1418-1425; 2001) through various mechanisms, leading to DNA modifications or mutations. Room fluorescent light has been found to generate phototoxic products including hydrogen peroxide (see Stoien et al., "Effect of near-ultraviolet and visible light on mammalian cells in culture II. Formation of toxic photoproducts in tissue culture medium by blacklight", Proc. Natl. Acad. Sci. USA 71:3961-3955; 1974; Wang et al., "Effect of room fluorescent light on the deterioration of tissue culture medium", In Vitro. 12:19-22; 1976; and Wang et. al., "Identification of hydrogen peroxide as a photoproduct toxic to human cells in tissue-culture medium irradiated with "daylight" fluorescent light", In Vitro. 14:715-722; 1978). Common media components such as tryptophan, tyrosine, pyridoxine and folic acid can enhance these reactions (see Grzelak et al., supra). The presence of serum in medium has historically minimized the problems caused by light-produced ROS. However, in the defined, serum-free or low-serum media commonly used in mammalian cell culture today, ROS-generated cytotoxicity can become more prevalent.

Media is applied to mammalian cells at a temperature of 37° C. to provide an ideal environment for cell metabolism to take place. Applying media at a temperature that is too low can shock the cells leading to inhibited metabolism or reduced viability. To avoid these problems cell culture media is usually warmed before it is applied to cells. Generally, cell culture medium is warmed in a water bath by immersing a container containing the medium into water in a "water bath" that has been pre-warmed to a pre-determined temperature. If small volumes of medium are needed, the technicians transfer a portion of the medium from the original container into a second sterile container (using sterile technique) or by warming the entire original bottle in the water bath. Currently the common practice is for cell culture technicians to estimate when the media inside the container has reached the proper temperature. This is usually done by timing or by touching the outside of the container to determine if it "feels" to be the proper temperature. If the technician incorrectly estimates the medium temperature the cells may be inhibited metabolically, have reduced viability or in extreme cases perish due to the shock caused by large variations in medium temperature over a short period of time.

Contamination may occur during the media-warming process because the media container is directly exposed to non-sterile water in the water bath. Bacteria, mold, yeast and other microorganisms present in the non-sterile water bath water remain on the outside of the media container and may be carried on the outside of the media container into a sterile environment, such as a biological safety cabinet, where the warmed media is transferred into cell cultures. Technicians usually minimize this hazard by washing the outside of the media bottle with sterilizing solutions such as 70% isopropyl alcohol.

What is needed is a way of storing and manipulating cell culture medium to avoid the problems outlined above.

SUMMARY OF THE INVENTION

A cell culture medium container assembly is disclosed with unique shrink-wrap light protection label that works as a light barrier to protect media from light damage.

A light sensitive medium container assembly is disclosed having a container with a removable cap that is configured to hold a light sensitive medium and a shrink-wrap label having one or more windows. The shrink-wrap label is configured to cover the exterior of the container and block harmful light to protect the light sensitive medium.

A light sensitive medium package kit is disclosed having a light sensitive medium, a container that is configured to hold the light sensitive medium, a shrink-wrap label having one or more windows and a temperature gauge proximate the container under said shrink-wrap label and viewable through one of the windows. The shrink-wrap label is configured to cover the exterior of the container to block harmful light to protect the light sensitive medium.

A method of making a light sensitive medium package kit is disclosed, the method includes providing a light sensitive medium, filling a container with the light sensitive medium, attaching a thermometer to the container, receiving an order for the light sensitive medium, generating a stick-on label corresponding to the order, attaching said stick-on label to the container, applying a shrink-wrap label over the container with the shrink-wrap label having a label window aligned with the stick-on label, and heating the shrink-wrap label to cover the container.

A shrink-wrap label is disclosed for use with a cell culture medium container, the shrink-wrap label including shrink-wrap material having light blocking properties, the shrink-wrap material being capable of covering the cell culture medium container, and one or more viewing windows in the shrink-wrap material.

BRIEF DESCRIPTION OF THE DRAWINGS

The following detailed description of the invention reference is made to the accompanying drawings which form a part hereof, and in which are shown, by way of illustration, specific embodiments in which the invention may be practiced. These embodiments are described in sufficient detail to enable those skilled in the art to practice the invention. Other embodiments may be utilized and changes may be made without departing from the scope of the present invention

DETAILED DESCRIPTION OF THE INVENTION

Figure 1:
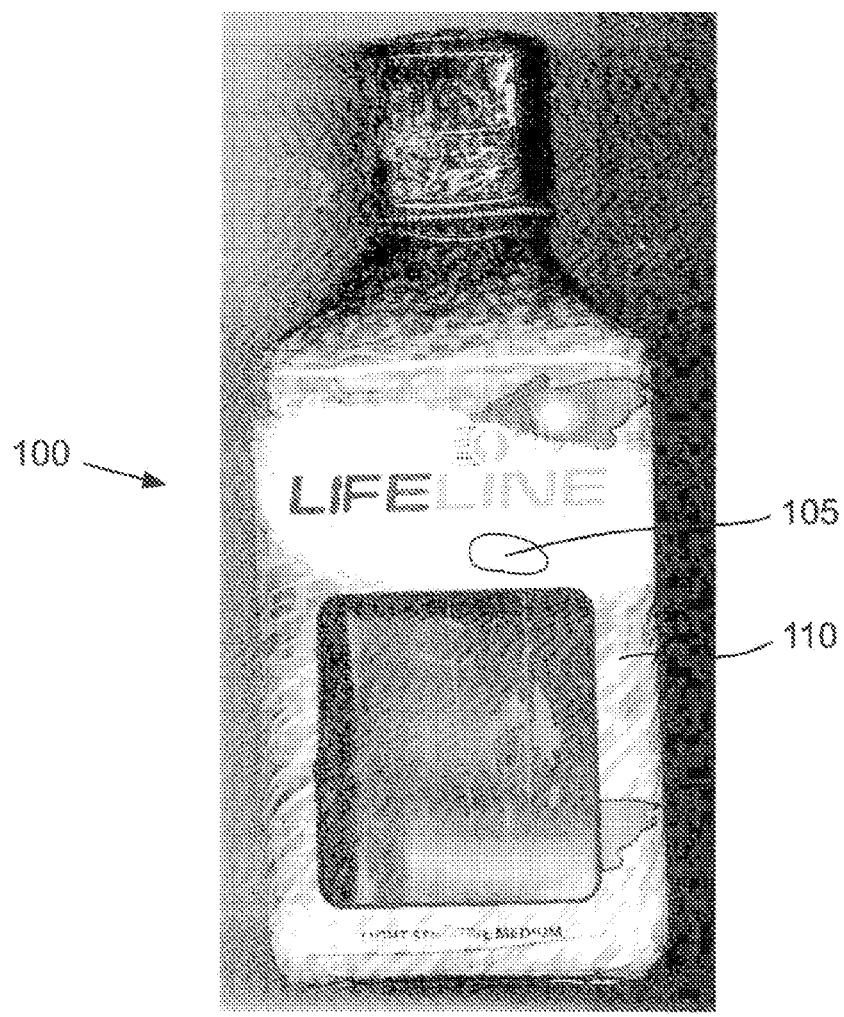
FIG. 1 is a front view of a cell culture medium container assembly according to one embodiment of the invention having a shrink-wrap light protection label with perforations around the cap area.
Figure 2:
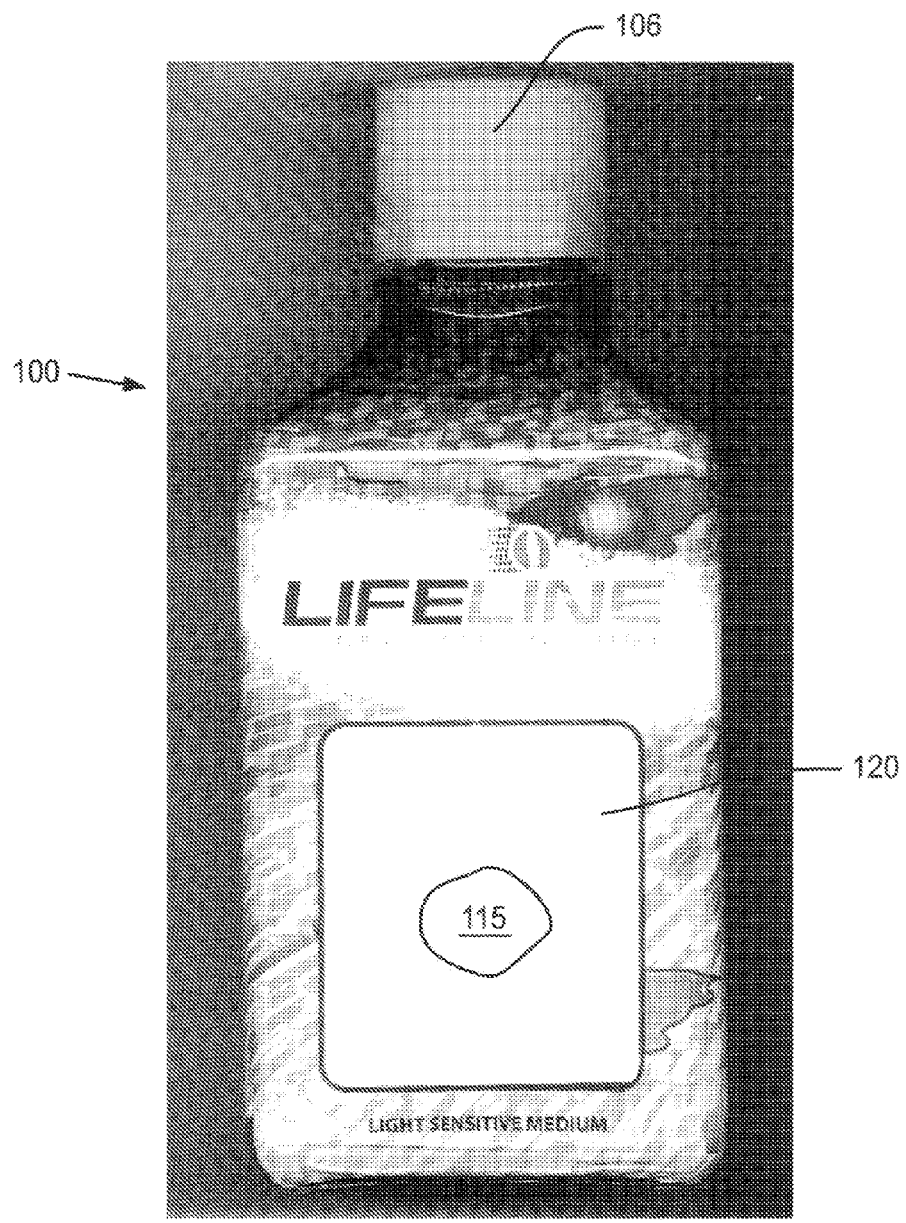
FIG. 2 is a front view of a cell culture medium container assembly of the cell culture medium container of FIG. 1 with the perforated cap portion of the shrink-wrap label removed.
Figures 3, 4:
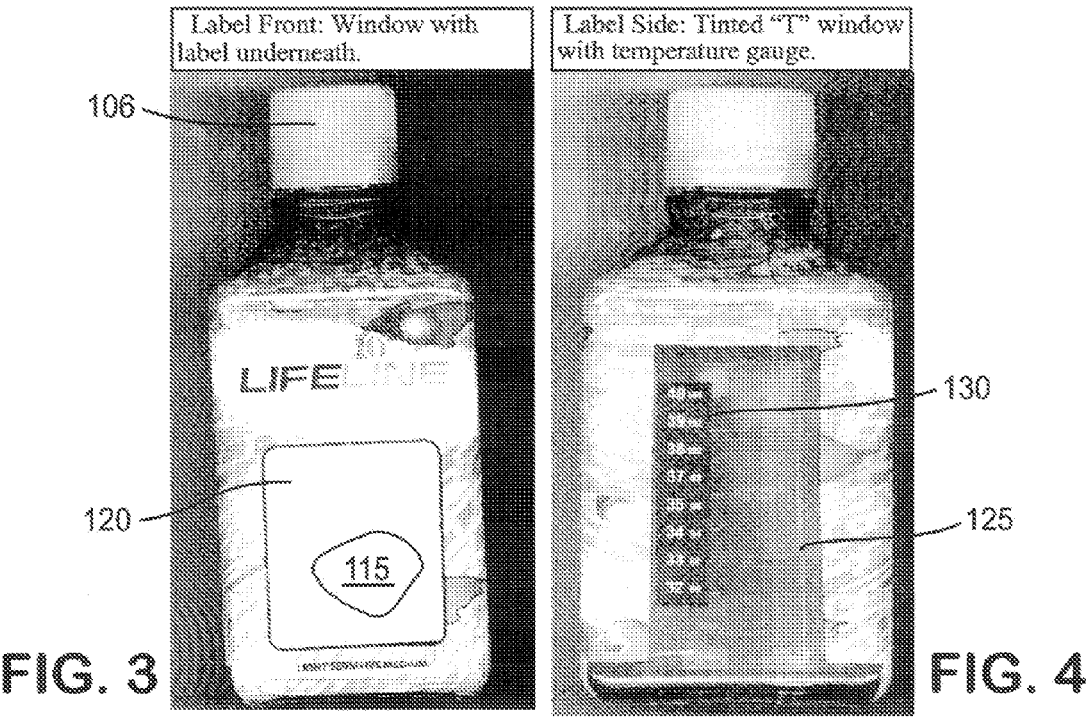
FIG. 3 is a front view of the cell culture medium container assembly of FIG. 2 showing a label window in the shrink-wrap label having for viewing a label underneath.
FIG. 4 is a side view of the cell culture medium container assembly of FIG. 2 showing a content window (or "T" window) in the shrink-wrap label for viewing the contents of the container, and a temperature gauge for monitoring the temperature.
Figures 5, 6:
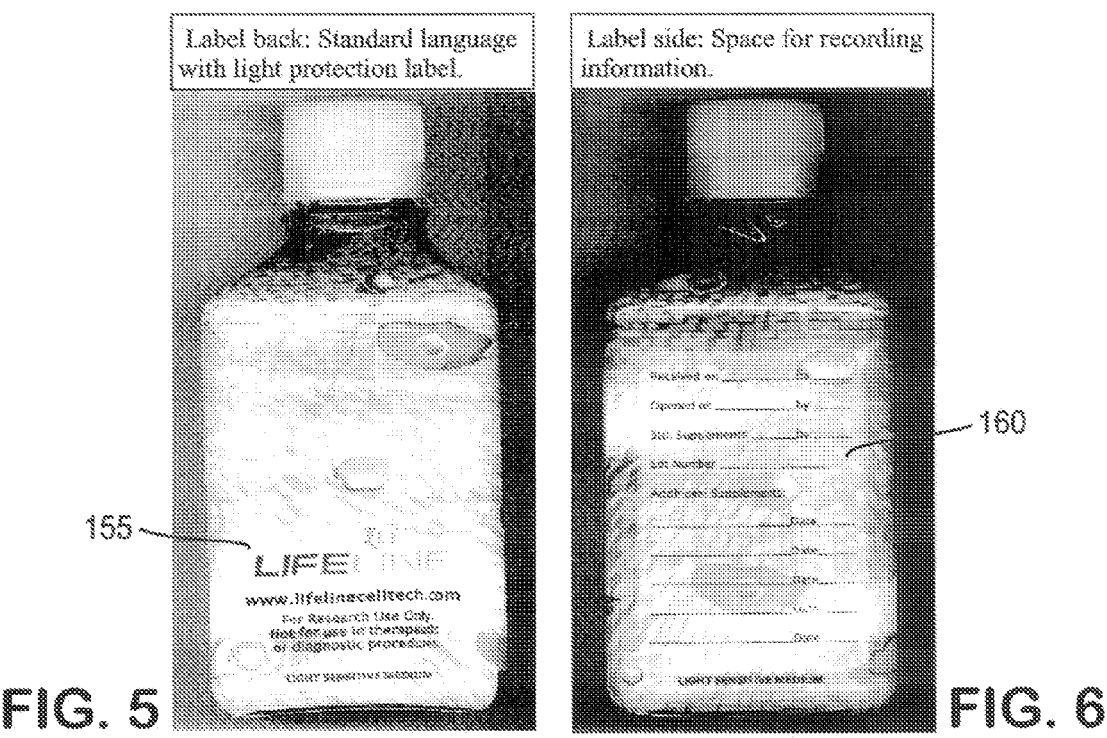
FIG. 5 is a back view of the cell culture medium container assembly of FIG. 2 showing language or instructions printed on the shrink-wrap label.
FIG. 6 is a side view of the cell culture medium container assembly of FIG. 2 showing space on the shrink-wrap label for recording information about the cell culture medium container.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The particular implementations shown and described herein are illustrative of the invention and its best mode and are not intended to otherwise limit the scope of the invention in any way. Indeed, for the sake of brevity, many conventional techniques related to shrink-wrap packaging, cell culture medium, clean room manufacturing, and other aspects of the example embodiments may not be described in detail herein.

The present invention provides significant improvements to traditional light sensitive media packaging. These improvements include A unique shrink-wrap label that works as a light barrier to protect media from light damage (one or more viewing windows may by slightly tinted with color to lessen light penetration).

A convenient built-in media temperature gauge that assists in contamination-free media warming.

The shrink-wrap label is designed to include ample space for writing important information.

Included in the shrink-wrap label design is a small viewing content window to check volume remaining within the container.

A special protective water bath bag/sleeve for use when placing the media container assembly in a water bath. The sleeve protects the bottle from contaminants found in the water bath.

FIGS. 1-6 show a cell culture medium container assembly 100 according to one embodiment of the invention having a container 105 with cap 106 covered with a shrink-wrap light protection label 110. The shrink-wrap label 110 fits over the container 105 to protect the contents of the container, such as light sensitive medium, from any harmful light. The shrink-wrap label 110 includes one or more viewing widows, described in more detail below.

The culture medium container assembly 100 is designed to protect many types of light sensitive medium. Examples include: any media containing riboflavin; RPMI 1640; Dulbecco's Minimal Essential Medium (DMEM); Ham's F-12; Waymouth's; William's E; MEM; EMEM; Medium 199; MCDB 131; McCoys 5A; Leibovitz's L-15; Iscove's; Modified Dulbecco's medium; Glasgow MEM; DMEM-F12; containing thiols or metal ions (such as ferric ions or cystine); Media; and Media containing compounds or chemicals that when exposed to light produce cytotoxic radicals, chemicals or compounds directly or through intermediate reactions with other components in the medium.

The container 105 may be any suitable shape and size, and may be made of PETG (Polyethylene Terephthalate Copolymer), PET (polyethylene terephthalate), Glass, Polycabonate or other materials compatible with the medium. One example of a suitable container is a Nalgene Labware 500 ml bottle, model 2019 Sterile Square Media Bottle, by Nalge Nunc International, Rochester, N.Y., U.S.A.

In one embodiment, a stick-on label 115 is attached directly to the container 105. The stick-on label 115 may include information about the contents container 105. This is important because if the user removes the shrink-wrap label 110, then the stick-on label 115 remains on the product, thus preventing the uncertainly caused by unmarked liquids. The shrink-wrap label 110 goes over the stick-on label 115. A label window 120 in the shrink-wrap label 110 allows the user to read the stick-on label 115 after assembly. The label window 120 may be clear or have a light protection tint.

In another embodiment the stick-on label 115 may be attached on top of the shrink-wrap label. The stick-on label 115 may include information about the contents container 105. In this embodiment, the shrink-wrap label 110 may not have a label window 120. If the shrink-wrap label 110 does have a label window 120, the stick-on label 115 may be placed over the window for blocking the light.

A content window 125 in the shrink-wrap label 110 allows the user to see the contents of the container 105 and how much is left. The content window 125 may have the shape of an inverted "T" that allows viewing into the bottom corner of a square media container. If the container 105 has fluid level markings, the content window 125 may be positioned over them for viewing. The content window 125 should have a light protection tint to protect the contents from harmful light.

A temperature gauge 130 may be positioned on the container 105, under the shrink-wrap label 110, in the content window 125. One embodiment of the temperature gauge 130 gives a reversible color change, meaning that when the proper temperature is reached the color becomes apparent—but the color goes away when the temperature changes. This process can happen over and over again. The technology uses a microencapsulated liquid crystal color changing ink and is made by TMC LLC (http://www.t-m-c.com/our_products.html) distributed to us by Dry Pak Industries (Studio City, Calif. www.drypak.com). The product is called a 16-Event reversible temperature label 90-120° F. (chopped version) (see http://www.t-m-c.com/16_level_vertical.html). In one embodiment, the thermometer 130 measures a temperature range between 32-40° C. In another embodiment, the thermometer 130 measures a temperature range between 0-8° C.

Figure 7:
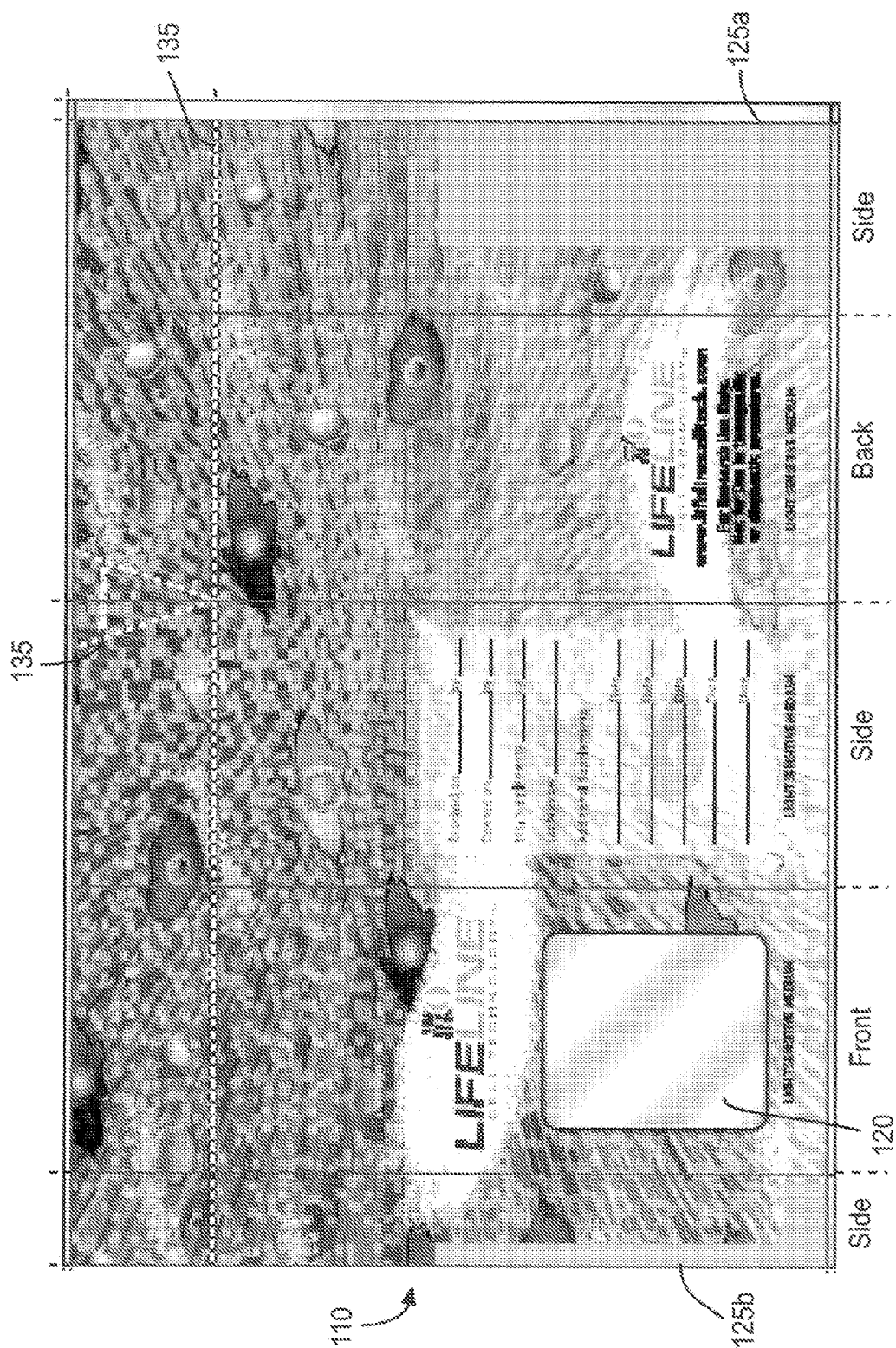
FIG. 7 is a plan view of one embodiment of a shrink-wrap label.

FIG. 7 shows a plan view of the shrink-wrap label 110 showing the label window 120 and the content window 125 (shown as 125a and 125b in the figure). The inverted "T" portion is positioned along a bottom portion of the shrink-wrap label 110 to allow viewing of the bottom of the container 105. The material for the shrink-wrap label 110 may be any suitable shrink-wrap material, such as polyolefin shrink films including PETG material and other materials that have shrink properties. The thickness of the shrink material may be 1 to 5 mm, preferably be 2 mm thickness. The shrink-wrap label may come in individually cut cylindrical sleeves, sheets or on a roll.

The shrink-wrap label 110 also includes perforations 135 along a top portion. The perforations 135 correspond to the cap area of the container 105 and preferably should be a "V" shape, but could be other shapes, on the vertical with a horizontal perforation going around the bottom of the cap. The shrink wrap label should overlap the top of the cap (after it has been shrunken) in order to provide a tamper-evident seal the breaking of which would provide evidence that the product may have been opened prior to receipt. The shrink-wrap label 110 includes many areas for writing information, such as company information 155, instructions or recording information 160 about the cell culture medium container. The ink that is used to print on the shrink-wrap label 110 should not contain chemicals that could leach though plastics (no phenols).

Figure 9:
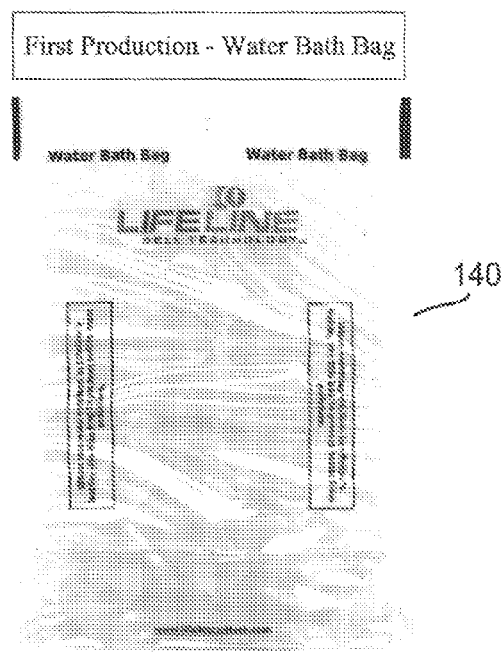
FIGS. 8 and 9 are views of a water bath bag for use with the cell culture medium container assembly of FIG. 1.
Figure 10:
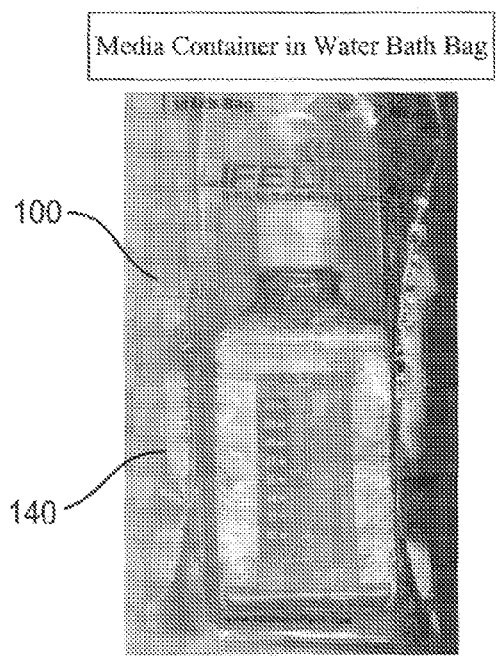
FIG. 10 is a view of the cell culture medium container assembly of FIG. 2 positioned in the water bath bag of FIGS. 8 and 9. the thermometer and contents are visible through the water bath bag.
Figure 8:
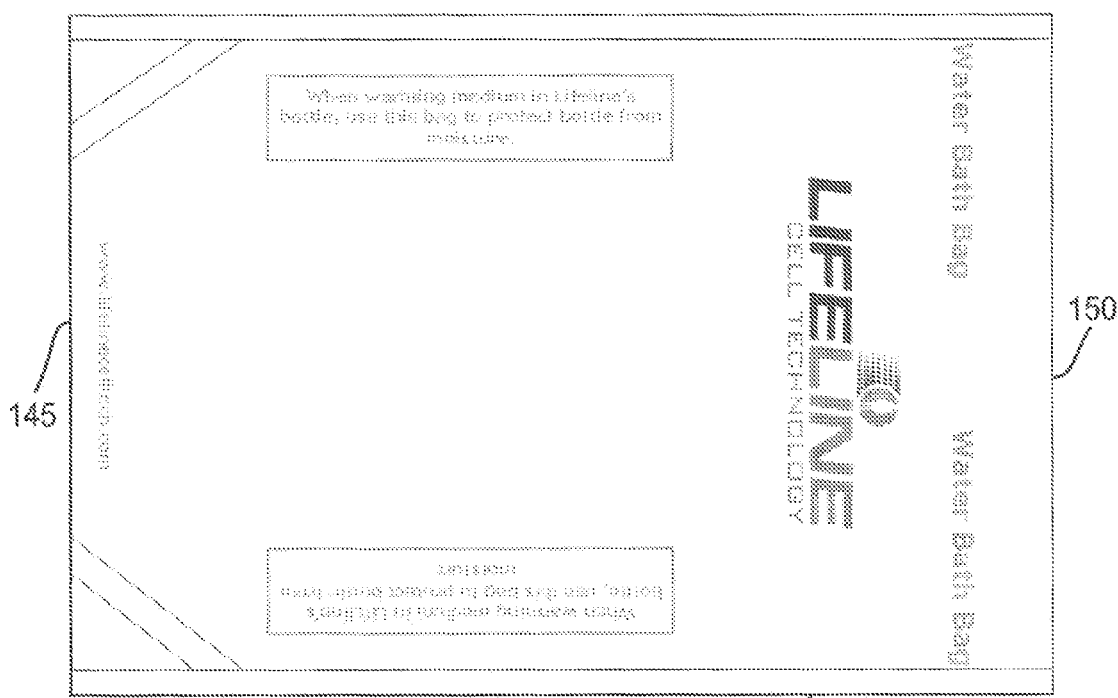

Another embodiment of the invention uses a water bath bag 140, shown in FIGS. 8-10. The water bath bag 140 is designed to be a "stand-up" pouch, with a closed lower end 145 and an open upper end 150 for insertion of the cell culture medium container assembly 100, shown in FIG. 10. The water bath bag 140 may be made of any suitable plastic material, such as 75 gauge PET or Nylon, that is clear for viewing the cell culture medium container assembly 100. It is important that the thermometer may be seen through the bag. The upper end 150 may be capable of closing, with a zipper (such as a zip lock) for storing or shipping the cell culture medium container assembly 100. The water bath bag 140 may also have printing in it, such as company information, instructions or warnings.

Below is one embodiment of assembly of the cell culture medium container assembly 100 and filling the container with light sensitive medium to create a light sensitive medium package kit.
1. The light sensitive medium is manufactured.
2. Filling a container, such as container 105, with the light sensitive medium. Attaching an appropriate temperature gauge, such as temperature gauge 130, to the container at a specific location (so it can be viewed when the shrink-wrap label is covering it). This can be done with automated labeling machines or manually with simple templates used as placement aids.
3. An order arrives for the light sensitive medium.
4. The computer generates a stick-on label, such as stick-on label 115, with product-specific information for the product ordered (i.e., light sensitive medium) with such things as product name, part number, lot number, manufacture date, expiration date, volume, application, customer name, storage temperature and other such product-specific information. This information can be loaded into a computerized labeling machine that prints the stick-on labels and applies them to a specific location on the container, or the process can be done manually by printing the stick-on label in one step and manually applying the labels during a second step.
5. A shrink-wrap label, such as shrink-wrap sleeve label 110, is then put over the medium container that has been labeled with the stick-on label. The shrink-wrap label must be precisely placed so the stick-on label shows through a label window and the product-specific information is visible. Note that if the shrink-wrap label is mistakenly removed, the stick-on label remains on the container so that the product is still labeled. This step can be done with automated machines or manually.
6. The medium container with the shrink-wrap label is put into a heated environment carefully controlled to apply the proper amount of heat for the proper amount of time that allows the shrink-wrap to shrink onto the container evenly and properly. This can be done in several ways:
    a. The labeled container can be put onto a rotating "turntable" and a person can manually blow hot air onto the rotating container with a heat gun to shrink down to shrink-wrap label onto the container.
    b. The labeled container can be put onto a conveyer belt and directed into a heated "shrink-tunnel." Once inside the heated tunnel the labeled container is subject to increased levels of heat and turbulent air flow causing the label to shrink down onto the container.
    c. Dry heat or steam can be used as a heat source.
7. The labeled product may then either be immediately shipped or stored for shipment on another day.

While the invention is described and illustrated here in the context of a limited number of embodiments, the invention may be embodied in many forms without departing from the spirit of the essential characteristics of the invention. The illustrated and described embodiments, including what is described in the abstract of the disclosure, are therefore to be considered in all respects as illustrative and not restrictive. The scope of the invention is indicated by the appended claims rather than by the foregoing description, and all changes that come within the meaning and range of equivalency of the claims are intended to be embraced therein.

I claim:

1. A light sensitive medium container assembly comprising:
    a container with a removable cap configured to hold a light sensitive medium;
    a shrink-wrap label having one or more windows comprising a light protective tint disposed over the entire area of the one or more windows, wherein one of said windows is an inverted "T" shape, the shrink-wrap label configured to cover the exterior of said container and block harmful light to protect said light sensitive medium;

a temperature gauge proximate said container under said shrink-wrap label and viewable through one of said windows; and a resealable protective sleeve disposed around the exterior of the container and label, the sleeve being impervious to liquid when sealed.

2. The assembly of claim 1, wherein said temperature gauge is configured to measure temperatures between about 32-40° C.

3. The assembly of claim 1, wherein said temperature gauge is configured to measure temperatures between about 0-8° C.

4. The assembly of claim 1, wherein one of said windows is configured to allow viewing of the content of said container.

5. The assembly of claim 1, further comprising a stick-on label.

6. The assembly of claim 5, wherein said stick-on label attached to said container under said shrink-wrap label, said stick-on label being viewable through one of said windows.

7. The assembly of claim 5, wherein said stick-on label attached to said container on top of said shrink-wrap label.

8. The assembly of claim 1, wherein said shrink-wrap label is made of PETG.

9. The assembly of claim 1, wherein at least a portion of said protective sleeve is transparent.

10. The assembly of claim 9, wherein said protective sleeve comprises printed instructions.

* * * * *